(12) United States Patent
La Fontaine

(10) Patent No.: US 6,603,543 B1
(45) Date of Patent: Aug. 5, 2003

(54) INSPECTION SYSTEM WITH ENHANCED CONTRAST

(75) Inventor: Bruno M. La Fontaine, Pleasanton, CA (US)

(73) Assignee: Advanced Micro Devices, Inc., Sunnyvale, CA (US)

( * ) Notice: Subject to any disclaimer, the term of this patent is extended or adjusted under 35 U.S.C. 154(b) by 0 days.

(21) Appl. No.: 09/774,000

(22) Filed: Feb. 1, 2001

(51) Int. Cl.[7] ............................................. G01N 21/00
(52) U.S. Cl. ................................. 356/237.5; 356/237.4
(58) Field of Search ........................ 356/237.4, 237.5, 356/394

(56) References Cited

U.S. PATENT DOCUMENTS

| | | | |
|---|---|---|---|
| 4,218,142 A | 8/1980 | Kryger et al. | |
| 4,392,120 A | 7/1983 | Mita et al. | |
| 4,547,895 A | 10/1985 | Mita et al. | |
| 4,595,289 A | 6/1986 | Feldman et al. | |
| 4,795,260 A | 1/1989 | Schuur et al. | |
| 4,943,734 A | 7/1990 | Johnson et al. | |
| 5,023,714 A * | 6/1991 | Lemelson | 348/125 |
| 5,278,012 A * | 1/1994 | Yamanaka et al. | 250/559.44 |
| 5,384,230 A | 1/1995 | Berg | |
| 5,486,919 A | 1/1996 | Tsuji et al. | |
| 6,002,740 A | 12/1999 | Cerrina et al. | |
| 6,014,209 A * | 1/2000 | Bishop | 356/237.5 |
| 6,091,488 A * | 7/2000 | Bishop | 356/237.5 |
| 6,208,421 B1 * | 3/2001 | Maris et al. | 356/432 |
| 2001/0052975 A1 | 12/2001 | Biellak et al. | |
| 2002/0027663 A1 | 3/2002 | Mueller-Rentz | |
| 2002/0034198 A1 | 3/2002 | Masuda | |
| 2002/0088952 A1 | 7/2002 | Rao et al. | |

* cited by examiner

Primary Examiner—Diane I. Lee
(74) Attorney, Agent, or Firm—Foley & Lardner

(57) ABSTRACT

An inspection tool or inspection system can be utilized to determine whether the appropriate pattern is on a reticle. The reticle can be associated with EUV lithographic tools. The system can utilize at least two pulse durations of light or an ultra-short pulse duration of light. The light is directed to the reticle and received by a detector.

20 Claims, 4 Drawing Sheets

INSPECTION SYSTEM WITH ENHANCED CONTRAST

CROSS REFERENCE TO RELATED APPLICATIONS

The present application is related to U.S. patent application Ser. No. 09/773,968, entitled, "Differential Wavelength Inspection of Reticles for EUV Lithography" filed by La Fontaine et al., (Atty. Dkt No. 39153-302) on an even date herewith and assigned to the assignee of the present application.

FIELD OF THE INVENTION

The present invention relates generally to an inspection system and an inspection method. More particularly, the present invention relates to an inspection system for and a method of inspecting a pattern on a reticle or photomask for defects and errors.

BACKGROUND OF THE INVENTION

Semiconductor fabrication techniques often utilize a mask or reticle. Radiation is provided through or reflected off the mask or reticle to form an image on a semiconductor wafer. The wafer is positioned to receive the radiation transmitted through or reflected off the mask or reticle. The image on the wafer corresponds to the pattern on the mask or reticle. The radiation can be light, such as ultraviolet light, vacuum ultraviolet (VUV) light, extreme ultraviolet light (EUV) and deep ultraviolet light. The radiation can also be x-ray radiation, e-beam radiation, etc.

One advanced form of lithography is extreme ultraviolet (EUV) light lithography. A conventional EUV system (e.g., an optical reduction camera or stepper) utilizes an EUV radiation source, a first EUV lens assembly (e.g., a condenser lens), an EUV reticle, and a second EUV lens assembly (e.g., an objective lens). EUV radiation can be created at the EUV radiation source and projected onto the EUV reticle. The EUV reticle is typically a resonant-reflective medium including a pattern of absorbing material.

The EUV reticle reflects a substantial portion of the EUV radiation which carries an integrated circuit (IC) pattern formed on the reticle to the second EUV lens assembly. The first and second lens assemblies can be an all resonant-reflective imaging system including an aspheric optical system at 4:1 demagnification (e.g., a series of high precision mirrors). EUV radiation reflected off the EUV reticle is provided from the second EUV lens assembly to a photoresist coated wafer.

EUV lithography utilizes radiation in a wavelength ranging from 5 to 70 nanometers (nm) (e.g., 11–14 nanometers). A conventional EUV reticle can be a multilayer medium including an absorber pattern across its surface. The multilayer medium can utilize molybdenum/silicon (Mo—Si) layers or molybdenum/beryllium layers (Mo—Be). The absorber pattern can be one or more layers of material selectively arranged on a top surface of the multilayer medium. The actinic wavelength for an EUV system can be 13.4 nm.

Tools, such as, masks or reticles, for lithographic IC fabrication processes must be inspected to ensure that the proper pattern is present on the reticle and to ensure that defects are not present on the reticle. Defects can be introduced during the fabrication of the mask or reticle, during handling of the mask or reticle, and/or during use of the reticle in the EUV lithographic system. Inspections can verify that the mask or reticle has the proper physical characteristics, critical dimensions, and registration.

Inspections ensure that the photoresist material can be selectively formed within specified tolerances. For example, mistakes or unacceptable process variations associated with the mask or reticle should be corrected before any physical changes are produced on the wafer itself, such as, by doping, etching, etc.

Various techniques can be utilized to inspect masks and reticles. For example, optical microscopes, scanning electron microscopes (SEMs) and laser-based systems have been utilized for inspection tasks and line width measurement tasks. Holographic principles have even been used to detect defects on masks and reticles.

The amount of automation in these inspection tasks has varied. For example, human vision may be required in some inspection procedures to determine and classify defects. Other inspection tasks have been automated so that the human operator is completely removed from the defect inspection tasks. Automated mask or reticle inspection systems include the KLARIS system manufactured by KLA, the Chipcheck system manufactured by Cambridge Instruments, and the 8100 XP-R CD SEM manufactured by KLA-Tencor Corp. Defect detection and pattern verification in these automated systems can be accomplished either by mask-to-mask or mask-to-standard comparisons.

One type of conventional automated defect detection system provides radiation or light from a light source to a surface of the mask or reticle being inspected. Light from the light source is directed through an optical system to the mask or reticle. The optical system focuses the light and can include mirrors, lenses, and prisms. The light strikes the surface of the reticle and is reflected. Alternatively, the light can pass through the mask.

The light reflected from the reticle or the light through the mask is sensed by photoelectric detectors. The light can be provided through an optical system including mirrors, lenses, and prisms. Generally, the light is analyzed to determine whether the appropriate image is on the reticle or mask and whether or not defects are present. Defects can include scratches, misalignment, line errors, contamination, dust, etc.

Conventional inspection systems utilizing conventional inspection pulse durations and wavelengths of light cannot adequately inspect EUV reticles or masks. EUV masks and reticles have a significantly different construction than reticles used in less advanced lithography. The contrast between the absorber pattern and the multilayer of the EUV reticle is poor at conventional inspection wavelengths and pulse durations. The contrast observed with conventional inspections systems has been fifty percent (50%) or less. Accordingly, ascertaining the correctness of the image on the EUV reticle as well as determining whether any defects are present on the EUV reticle is difficult with conventional inspection systems.

Thus, there is a need for a highly accurate inspection system that can be utilized to detect defects and patterns on a mask or reticle. Further, there is a need for a semiconductor fabrication inspection tool for detecting defects and patterns on an EUV reticle. Even further still, there is need for a system for or a method of detecting patterns on an EUV reticle which obtains enhanced contrast and greater inspection functionality capability. Even further still, there is a need for an inspection tool and inspection method that is capable of reliably detecting patterns on an EUV reticle and capable of greater inspection capability. Yet further still

3 there is a need for a modification to a conventional inspection system that allows it to effectively inspect EUV reticles.

SUMMARY OF THE INVENTION

An exemplary embodiment relates to an inspection system. The inspection system is used with a reticle including a multilayer and an absorbing pattern. The inspection system includes a light source and a detector. The light source provides an ultra-short pulse duration of the light. The detector is positioned to receive the light after the light is reflected off the reticle.

Another exemplary embodiment relates to a method of inspecting a reticle. The reticle is associated with the manufacture of an integrated circuit. The method includes providing radiation at a first pulse duration to the reticle and receiving the radiation at the first pulse duration reflected from the reticle. The method also includes providing radiation at a second pulse duration to the reticle and receiving the radiation at the second pulse duration reflected from the reticle.

Still another exemplary embodiment relates to an inspection system for an EUV reticle for use in an integrated circuit fabrication system. The inspection system includes means for providing radiation at a first pulse duration to the reticle and means for detecting the radiation at the first pulse duration reflected off the reticle. The first pulse duration is an ultra-short pulse duration.

Yet another embodiment relates to an inspection system for an EUV reticle for use in an integrated circuit fabrication system. The inspection system includes means for providing radiation at a first pulse duration to the reticle and means for detecting the radiation at the first pulse duration reflected off the reticle. The inspection system further includes a means for providing radiation at a second pulse duration to the reticle, means for receiving the radiation at the second pulse duration reflected off the reticle, and means for comparing the reflected radiation at the first pulse duration to the reflected radiation at the second pulse duration.

BRIEF DESCRIPTION OF THE DRAWINGS

The present invention will hereafter be described with reference to the accompanying drawings, wherein like numerals denote like elements, and.

DETAILED DESCRIPTION OF THE PREFERRED EMBODIMENTS

Figure 1:
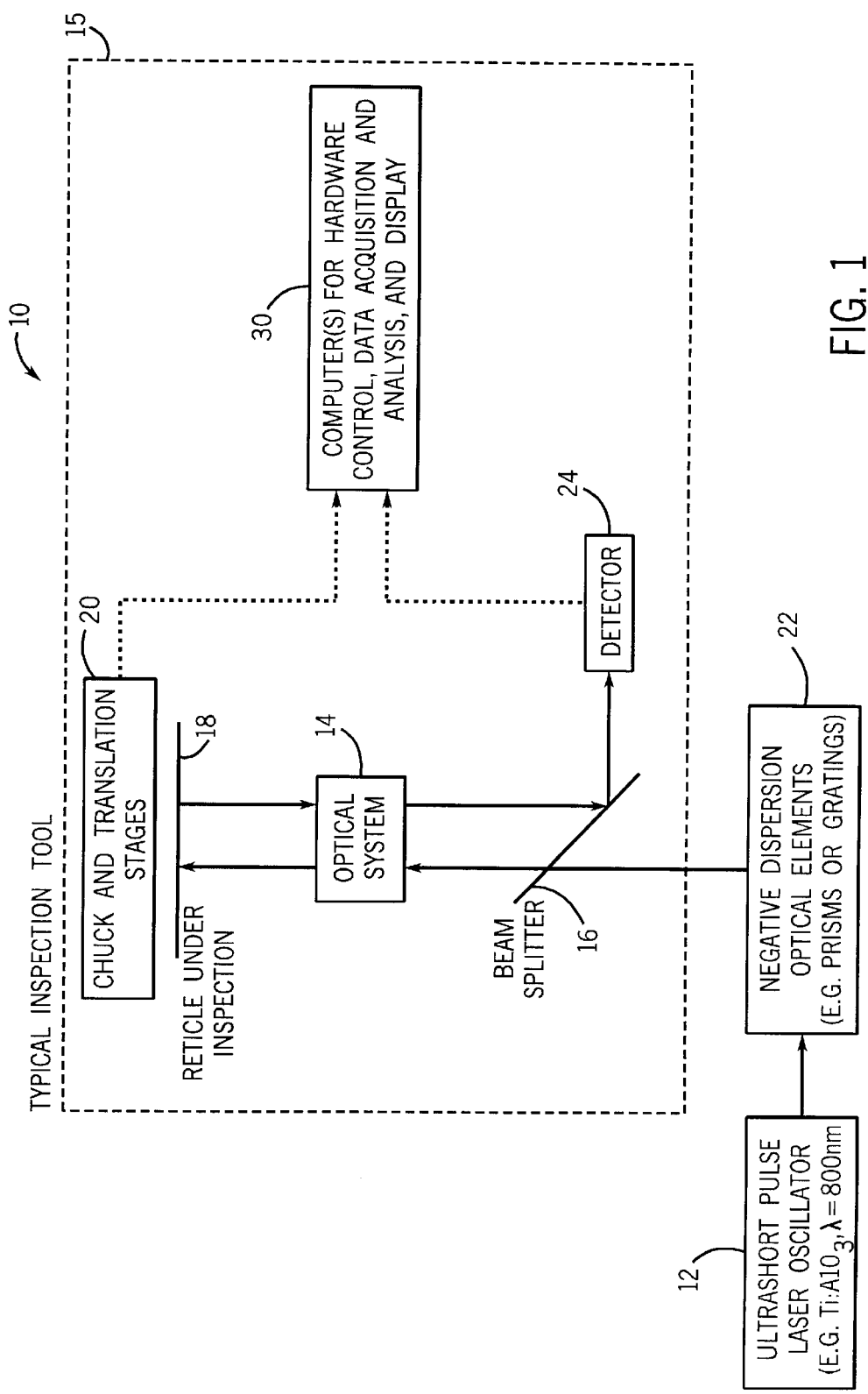
FIG. 1 is a general schematic block diagram of an inspection system for inspecting a mask or reticle in accordance with an exemplary embodiment.

With reference to FIG. 1, an inspection system 10 is configured to analyze the lithographic pattern (e.g., the absorber or reflector pattern) associated with a mask or reticle 18. Mask or reticle 18 can be any tool for use in integrated circuit (IC) lithographic equipment. System 10 advantageously achieves a higher contrast of an advanced lithographic pattern than possible with conventional inspection tools.

System 10 can detect defects or errors associated with reticle 18. For example, system 10 can be utilized to determine if defects manifested in a variety of forms including foreign matter, dust, scratches, bubbles, striations, steps, or other improper structures are provided on reticle 18. In addition, system 10 allows mask or reticle 18 to be inspected to determine that the appropriate absorber pattern or reflective pattern has been provided on reticle 18. System 10 can ensure that critical dimensions on reticle 18 are within tolerances.

Reticle 18 is preferably a lithographic tool for use in extreme ultraviolet (EUV) light lithography, wherein radiation having wavelengths less than 70 nm is utilized (most preferably, between 5 and 14 nm). For example, radiation or ultraviolet light at a wavelength of 13 nm can be reflected off reticle 18 to a semiconductor wafer coated with a photoresist. Alternatively, reticle 18 can be employed at other locations with respect to the EUV or advanced lithographic system.

Inspection system 10 includes a light source 12, an optical system 14, a beam-splitter 16, a stage 20, negative dispersion system 22, a detector 24, and a computer 30. System 10 is configured to provide radiation through optical system 14, off reticle 18, and to detector 24. System 10 can include a variety of conventional optical equipment arranged in a variety of configurations. Preferably, system 10 can provide automated analysis of reticle 18 on a display. Alternatively, system 10 can be utilized to enhance manual visual analysis of reticle 18, such as, through a microscope.

Computer 30, detector 24, optical system 14 and stage 20 can be components from a conventional system (e.g., within a dashed line 15 of FIG. 1). The conventional system can be modified to include light source 12 and negative dispersion system 22 configured to provide ultra-short pulse durations of laser light. Light source 12 is preferably an ultra-short pulse laser source. Negative dispersion system 22 preferably includes laser oscillator prisms or gratings for adjusting the pulse duration of light provided to reticle 18. In this way, a conventional system is modified to advantageously achieve multi-photon contrast enhancement according to one embodiment.

Light source 12 can be any number of sources of electromagnetic radiation. Light source 12 can be a single light source or multiple light sources for providing radiation at two or more pulse durations to reticle 18. Light source 12 can be an Ti:AlO$_3$, laser tuned at a wavelength of 800 nm. Alternatively, light source 12 can be an excimer laser, an ND:YAG laser, a frequency multiplied ND:YAG laser, or other light sources. Light source 12 can provide light at any number of wavelengths outside of the EUV wavelength ranges.

Light source 12 and negative dispersion system 22 cooperate to provide light at an ultra-short pulse duration ($\tau_s$). According to one embodiment, system 10 provides multiphoton microscopy by providing ultra-short pulses of light to reticle 18. The ultra-short pulses of light can have a pulse duration ($\tau_s$) of less than 1 picosecond (ps). The use of the ultra-short pulse duration produces high peak photon densities which cause simultaneous absorption of two or more photons on the absorptive portions with respect to reticle 18. Negative dispersion system 22 advantageously controls the laser pulse chirp to reticle 18. System 22 can include prisms, gratings, or other optical elements that control the pulse duration ($\tau_s$). The contrast of reticle 18 is increased due to this simultaneous absorption of two or more photons. According to an alternative embodiment, the reflective portions can have enhanced multi-photo absorption relative to the reflective portions. Reflective and absorptive portions of reticle 18 are described in more detail below with reference to FIG. 2.

According to an alternative embodiment, a differential technique is utilized to enhance contrast. The differential technique successively provides light to reticle 18 at a first pulse duration ($\tau_1$) followed by light at a second pulse duration ($\tau_2$). First pulse duration ($\tau_1$) and second pulse duration ($\tau_2$) can be ultra-short pulse durations or more conventional longer pulse durations. According to this embodiment, system 10 provides light or radiation at a first pulse duration ($\tau_1$) followed by light or radiation at a second pulse duration ($\tau_2$). Preferably, the first and second pulse durations ($\tau_1$ and $\tau_2$) of light provided by light source 12 are at a different wavelength than the light utilized by the EUV lithographic system. For example, if reticle 18 is designed to be utilized in a EUV lithographic system utilizing radiation at a wavelength of 13 nm, light source 12 preferably provides light at wavelengths not equal to 13 nm.

Light provided from light source 12 is reflected off reticle 18 in accordance with the pattern on reticle 18, to optical system 20. Optical system 20 provides the reflected light to detector 24 which provides an indication of the image at the first pulse duration ($\tau_1$) and an indication of the image at the second pulse duration ($\tau_2$) to computer 30. Computer 30 analyzes the images to inspect reticle 18 for defects.

Detector 24 can be a laser-light detector, a photo detector, a photo cell or other devices for converting a light signal to an electric signal. Detector 24 can include circuitry for converting the electric signal to a digital word or data. In one embodiment, detector 24 can be an array of photo detectors. In addition, detector 24 can be integrated with computer 30. Detector 24 can also be configured to provide the subtraction function for the alternative embodiment.

Computer 30 receives the electric signal from detector 24. Computer 30 can inspect for defects by comparing the image associated with the electric signal to a library of images stored in a memory or in a data base.

In the alternative embodiment in which system 10 utilizes a differential detection scheme, computer 30 receives the electric signal from detector 24 and determines whether a pattern 32 on reticle 18 is appropriate by analyzing the difference of the light received by detector 24 at the first and second pulse durations ($\tau_1$ and $\tau_2$). For example, computer 30 can compare the difference to a library of images stored in memory or in a database. Computer 30 can be a personal computer (PC), a workstation, a software control device, or other systems capable of analyzing signals from detector 24. Advantageously, system 10 is not susceptible to problems associated with low contrast present in conventional systems. Due to the use of at least two pulse durations ($\tau_1$ and $\tau_2$), computer 30 maximizes contrast.

Reticle 18 is advantageously designed with materials that have particular reflective characteristics at the ultra-short pulse duration ($\tau_s$) Reticle 18 is also fully designed so that the absorptive materials have relatively low reflective characteristics at the ultra-short pulse duration ($\tau_s$) As described in greater detail with reference to FIG. 2 below, reticle 18 includes a pattern 32 and a substrate 34. Reticle 18 can be a variety of shapes and sizes depending upon circuit requirements and lithographic tool designs. Pattern 32 has reflective portions and absorptive portions.

In the alternative embodiment in which system 10 utilizes a differential detection scheme, reticle 18 is advantageously designed with materials that have particular reflective characteristics and in which the reflective portions or the absorptive portions have relatively greater reflective characteristics at the first pulse duration ($\tau_1$) than at the second pulse duration ($\tau_2$). The materials of reticle 18 are chosen so that either:

(1) the intensity of light reflected off of the absorptive portions is approximately equal at the first and second pulse durations ($\tau_1$ and $\tau_2$) and yet the intensity of light reflected off the reflective portions is different at the first pulse duration ($\tau_1$) than at the second pulse duration ($\tau_2$); or (2) the intensity of light reflected off the reflective portions is approximately equal at the first and second pulse durations ($\tau_1$ and $\tau_2$) and yet the intensity of light reflected off the absorptive portions is different at the first pulse duration ($\tau_1$) than at the second pulse duration ($\tau_2$)

Accordingly, the intensity (I) of light reflected of reticle 18 can be represented mathematically as follows:

$$I_{at\ 1,\ ABS} = I_{at\ 2,\ ABS} \text{ and } I_{at\ 1,\ REFL} \neq I \text{ at } 2_{1,\ REFL}; \quad (1)$$

or $$I_{at\ 1,\ ABS} \neq I_{at\ 2,\ ABS} \text{ and } I_{at\ 1,\ REFL} = I_{at\ 2,\ REFL}. \quad (2)$$

Where $I_{at\ 1\ ABS}$ is the intensity of light at the first pulse duration ($\tau_1$) reflected off absorptive portions of reticle 18; $I_{at\ 2,\ ABS}$ is the intensity of light at the second pulse duration ($\tau_2$) reflected off absorptive portions of reticle 18; $I_{at\ 1,\ REFL}$ is the intensity of light at the first pulse duration ($\tau_1$) reflected off the reflective portions of reticle 18; and $I_{at\ 2,\ REFL}$ is the intensity of light at the second pulse duration ($\tau_2$) reflected off the reflective portions of reticle 18.

Computer 30 advantageously subtracts the intensity of light off reticle 18 received at the first pulse duration of light ($I_{at\ 1,\ ABS} + I_{at,\ REFL}$) from the intensity of light off reticle 18 received at the second pulse duration of light ($I_{at\ 2,\ ABS} + I_{at\ 2,\ REFL}$) to obtain a higher contrast ratio. Computer 30 can receive the entire image associated at the first pulse duration of light and subtract that entire image from the image received at the second pulse duration of light. Alternatively, computer 30 can sequentially subtract the intensity as received at various points or portions of reticle 18.

When the images are subtracted, the contrast is enhanced. Contrast is the ratio of light from the reflective portions to light from the absorptive portions. For example, contrast, C, can be mathematically defined as:

$$C = ABS\left|\frac{\Delta R_{ABS} - \Delta R_{REFL}}{\Delta R_{ABS} + \Delta R_{REFL}}\right|$$

where $\Delta R_{ABS} = I_{at\ 1,\ ABS} - I_{at\ 2,\ ABS}$; and $\Delta R_{REFL} = I_{at\ 1,\ REFL} - I_{at\ 2,\ REFL}$.

When the absorptive portions or reflective portions have a reflectance that is the same at the first and second pulse durations, ($\tau_1$ and $\tau_2$), $\Delta R_{ABS}$ equals zero and the contrast is maximized (e.g., C equals one). For example, if $\Delta R_{ABS}$ equals zero, the contrast, C, equals the absolute value of $\Delta RE_{REFL}/\Delta R_{REFL1}$ which equals one. The same result is obtained if $\Delta R_{REFL}$ is set to zero and $\Delta R_{ABS}$ is not equal to zero.

Figure 2:
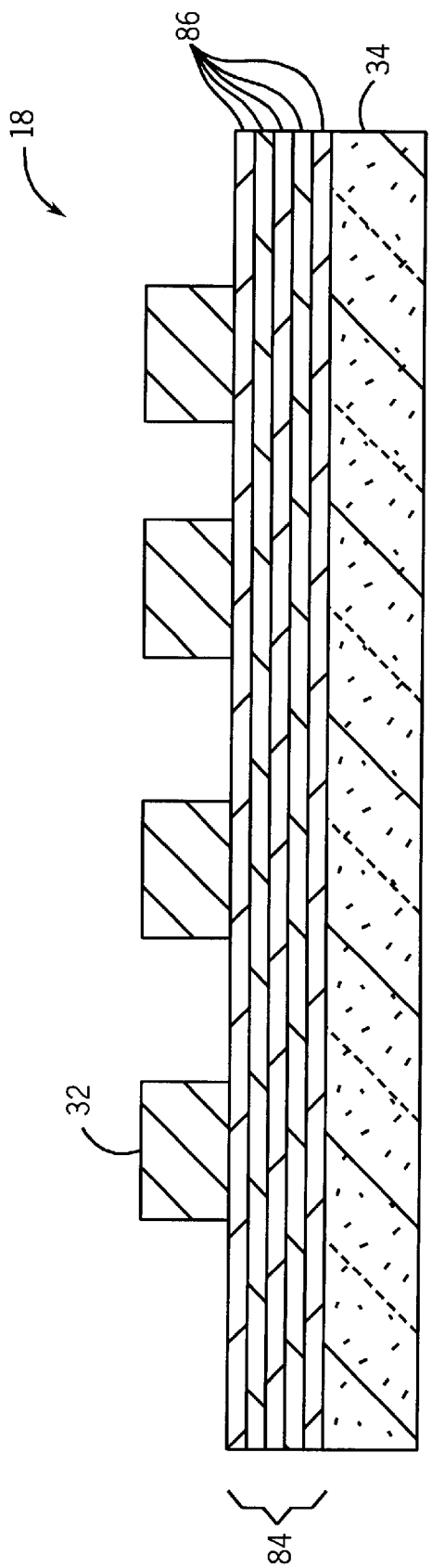
FIG. 2 is a more detailed schematic cross-sectional view of the reticle illustrated in FIG. 1.

With reference to FIG. 2, reticle 18 includes a substrate 34 and absorptive material 32. Substrate 34 includes a multi-layer 84 comprised of individual layers 86. Substrate 34 can include a low thermal expansion (LTE) base or silicon base. The LTE base can be an ultra-low expansion (ULE) glass manufactured by Corning.

Layers 86 of multilayer 84 can be alternating layers of molybdenum/beryllium (Mo—Be) films which are configured for maximum reflectance in the EUV band (e.g., 13 nanometer pulse duration). Alternatively, layers 86 can be molybdenum/silicon (Mo—Si) layers configured for maximum reflectance in the EUV band.

A pair of layers 86 can be 7 nm thick. Multilayer 84 can include forty pairs of layers 86 and can have a total thickness of 300 nm. Multilayer 84 can be manufactured by Osmic.

Absorptive material 32 can be a metal containing material, such as, chromium, chromium oxide, titanium nitride, tantalum nitride or other reflective material. Material 32 can be 50 nanometer thick. Absorptive material 32 is selectively formed on multilayer 84 to form a pattern. The selective formation can be accomplished by a lithographic process. Material 32 can be arranged in any pattern utilized to form an IC.

According to one embodiment that utilizes the differential inspection techniques, multilayer 84 has the same reflective characteristics at the first pulse duration ($\tau_1$) as at the second pulse duration ($\tau_2$). Absorptive material 32 is chosen to have different reflective characteristics at the first pulse duration ($\tau_1$) and at the second pulse duration ($\tau_2$) The first pulse duration ($\tau_1$) can be 0.1 picosecond and the second pulse duration ($\tau_2$) can be 10 nanoseconds.

In another embodiment of the differential inspection embodiment, absorptive material 32 is chosen to have different reflective characteristics at the first pulse duration ($\tau_1$) than at the second pulse duration ($\tau_2$), and multilayer 84 is chosen to have the same reflective characteristics at the first pulse duration ($\tau_1$) and the second pulse duration ($\tau_2$)

Figure 3:
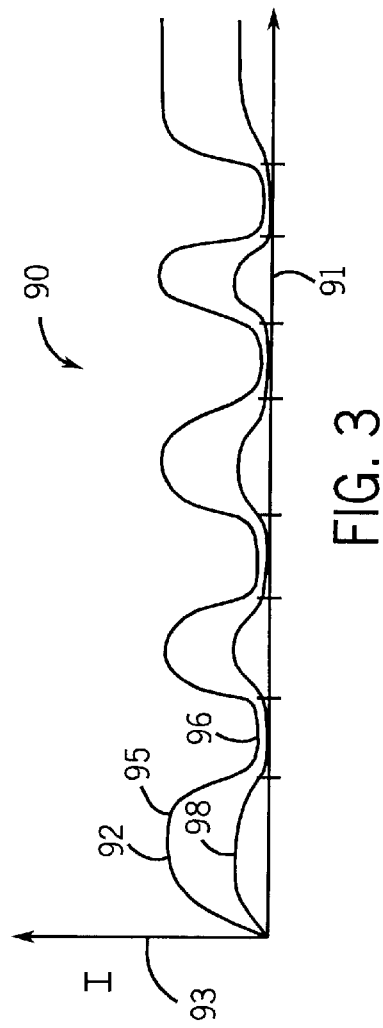
FIG. 3 is a graph showing the intensity of light reflected off the reticle illustrated in FIG. 2 when light at an ultra-short pulse duration is provided by the inspection system illustrated in FIG. 1.

With reference to FIGS. 1, 2 and 3, the image received by detector 24 is represented by a graph 90 (FIG. 3). The X-axis 91 of graph 90 represents the position on reticle 18 (FIG. 2), and the Y-axis 93 represents the intensity of light reflected from reticle 18. A line 92 represents the intensity of light reflected off reticle 18 when light source 12 and negative dispersion system 22 provides an ultra-short pulse duration ($\tau_s$). As can be seen from FIG. 3, line 92 shows a considerable contrast between a peak 95 associated with reflective portions and a trough 96 associated with absorptive portions. A line 98 represents light reflected off reticle 18 using a continuous light source or c.w. laser.

Figure 4:
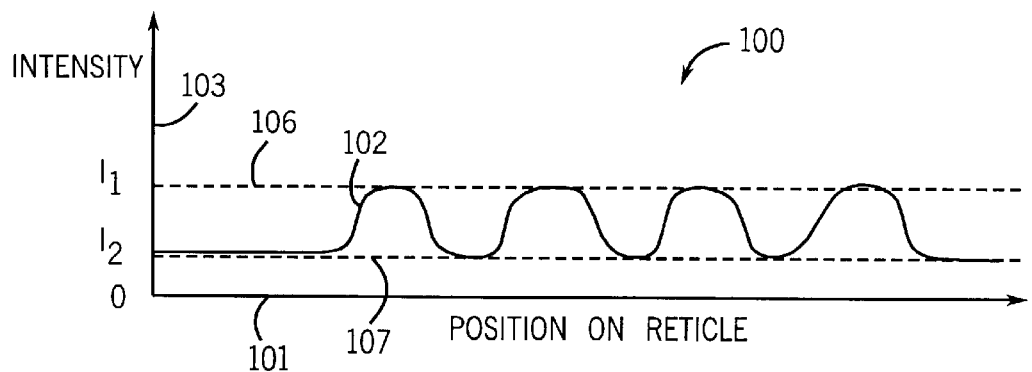
FIG. 4 is a graph showing the intensity of light reflected off a reflective portion and off an absorptive portion of the reticle illustrated in FIG. 2 when light at the first pulse duration ($\tau_1$) is provided to the reticle.
Figure 5:
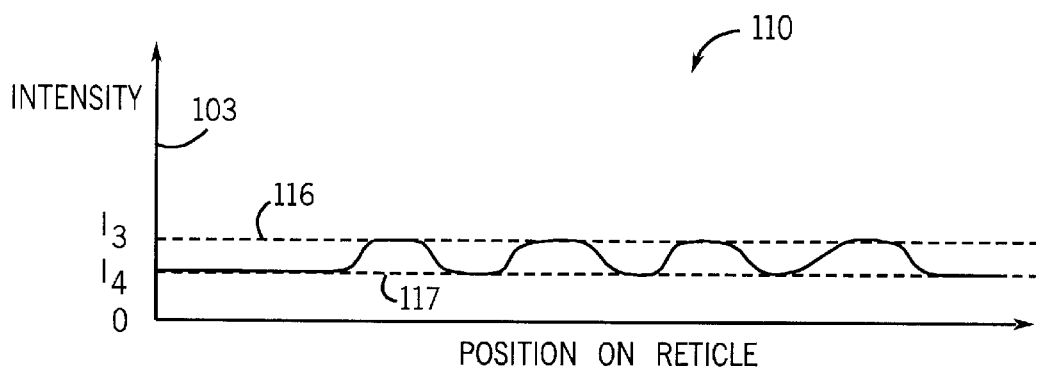
FIG. 5 is a graph showing the intensity of light reflected off a reflective portion and off an absorptive portion of the reticle illustrated in FIG. 2 when light at the second pulse duration ($\tau_2$) is provided to the reticle.

With reference to FIGS. 4 and 5, the image received at detector 24 (FIGS. 2 and 3) is represented by graphs 100 and 110 when system 10 uses the differential inspection scheme. X-axes 101 of graphs 100 and 110 represent the position on reticle 18, and Y-axes 103 of graphs 100 and 110 represent intensity of light reflected from reticle 18.

Graph 100 includes a solid line 102 representative of the intensity of light at the first pulse duration ($\tau_1$) (e.g., the ultra-short pulse duration) reflected from multilayer 84 (reflective portions) of reticle 18. As can be seen on graph 100, the reflective portions of the reticle provide an intensity ($I_1$) associated with the first pulse duration ($\tau_1$) (intensity value 106). Also, the intensity of the light reflected off the absorptive portions at the first pulse duration ($\tau_1$) is $I_2$ (intensity value 107).

In FIG. 5, graph 110 illustrates the intensity distribution reflected off the reticle at the second pulse duration ($\tau_2$). The intensity reflected off the reflective portions of reticle 18 is $I_3$ (intensity value 116) and that reflected off the absorptive portions is $I_4$ (intensity value 117). The value of the light intensity $I_4$ is similar to the value of the light intensity $I_2$.

Another embodiment would include absorptive material with essentially equal reflective characteristics at both the first pulse duration ($\tau_1$) and the second pulse duration ($\tau_2$) while multilayer 84 (i.e., the reflection portions) has different reflective characteristics at first and second pulse durations ($\tau_1$ and $\tau_2$)

Figure 6:
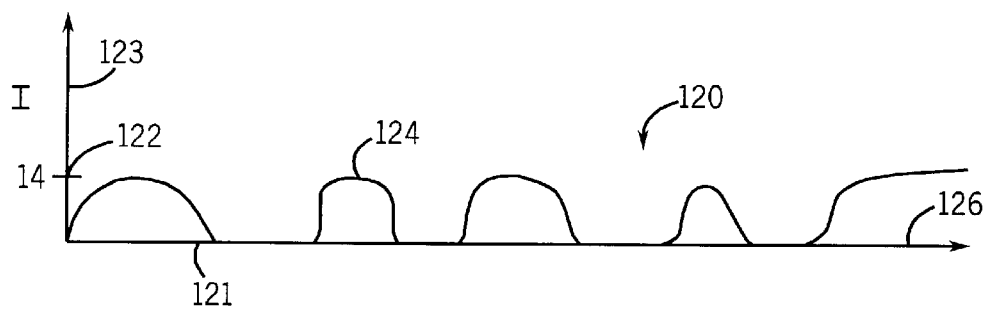
FIG. 6 is a graph showing the difference in the intensity of light at the first pulse duration ($\tau_1$) illustrated in FIG. 4 and the intensity of light at the second pulse duration ($\tau_2$) illustrated in FIG. 5.

With reference to FIG. 6, graph 100 can be subtracted from graph 110 to obtain a graph 120. Graph 120 is provided on an X-axis 121 and a Y-axis 123. Y-axis 123 represents intensity of light reflected off reticle 18 and X-axis 121 represents a position on reticle 18. Graph 120 includes a line 124 representative of the difference between lines 102 (FIG. 4) and 112 (FIG. 5). Graph 120 shows maximum intensity difference $I_5$ ($I_{5=I1}-I_3$, a point 122). A dashed line 126 represents the subtraction of line 104 and 114 which is approximately zero. Accordingly, graph 120 represents greater contrast associated with the image on reticle 18.

Figure 7:
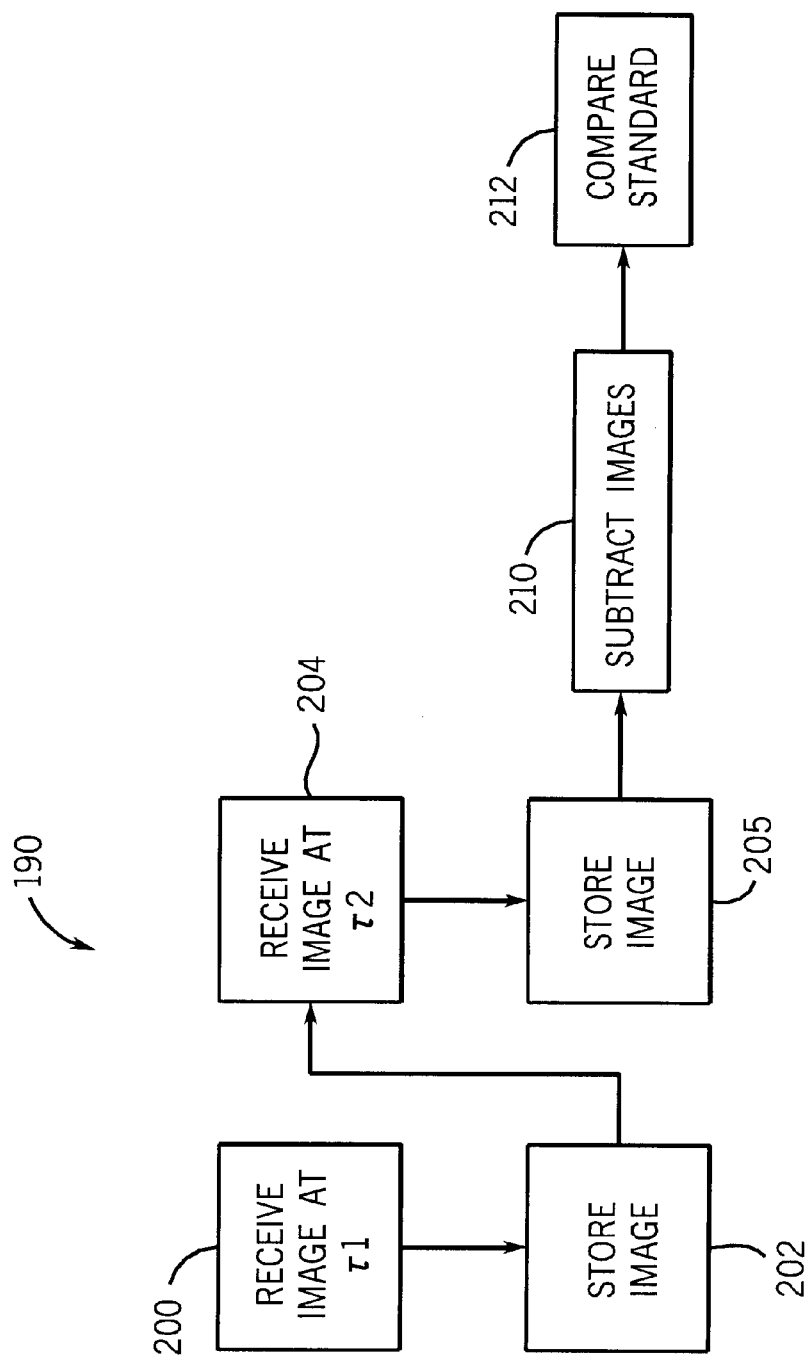
FIG. 7 is a flow diagram showing the operation of the inspection system illustrated in FIG. 1 in accordance with still another exemplary embodiment.

With reference to FIG. 7, the operation of system 10 is described with reference to FIGS. 1–6 according to a flow diagram 190 demonstrating the differential detection scheme. At a step 200, system 10 receives light at the first pulse duration ($\tau_1$) at detector 24. Detector 24 provides an electrical indication of the image on reticle 18 e.g., graph 100). The image from detector 24 is stored at a step 202 by computer 30.

At a step 204, light source 12 and system 22 provide light at the second pulse duration ($\tau_2$) to reticle 18. The image at the second pulse duration is received by detector 24 (e.g., graph 110).

At a step 206, the image received from detector 24 representative of the image at the second pulse duration ($\tau_2$) is stored by computer 30. At a step 210, computer 30 subtracts the image stored at step 202 from the image stored at step 206 to achieve higher contrast (e.g., graph 120). At a step 212, computer 30 compares the subtracted images to a standard image.

The standard image is associated with the acceptable specification tolerances for reticle 18. The standard image can be based upon an actual reticle which is known to function properly, based upon a prediction of what a working reticle should look like, or other design parameters. Computer 30 can also compare the signal to libraries of images to determine what types of errors are included on reticle 18. These errors can be classified and located. In an alternative embodiment, the subtracted images of step 210 can be viewed on a display screen.

According to a non-differential detection scheme, system 10 can operate according to diagram 190. However, the first pulse duration ($\tau_1$) is an ultra-short pulse duration and steps 204, 206, and 210 are omitted. Computer 30 can compare the image associated with the ultra-short pulse duration to standard images at step 212.

It is understood that while preferred embodiment and specific examples are given, they are for the purpose of illustration only and is not limited to the precise details disclosed. For example, although specific pulse durations of light are described, other types of light can be utilized. Further, although two pulse durations are discussed, different pulse durations and more than two pulse durations can be utilized. Various modifications may be made in the details within the scope and range of the equivalence of the claims without departing from what is claimed.

What is claimed is:

1. An inspection system for a reticle including a multilayer and an absorbing pattern, the inspection system comprising:

a light source; and a detector, wherein the light source provides light at an ultra-short pulse duration of the light, wherein the detector is positioned to receive the light at the first pulse duration and the light after the light is reflected off the reticle, wherein the light source provides a second pulse duration of the light, wherein the reticle includes a reflective portion and an absorber portion, wherein either the absorber portion has a different reflective characteristic at the ultra-short pulse duration and the second pulse duration and the reflective portion has a similar reflective characteristic at the ultra-short pulse duration and the second pulse duration, or the reflective portion has a different reflective characteristic at the ultra-short pulse duration and the second pulse duration and the absorber portion has a similar reflective characteristic at the ultra-short pulse duration and the second pulse duration.

2. The inspection system of claim 1, further comprising an analyzer coupled to the detector.

3. The inspection system at claim 2, wherein the light source sequentially provides the second pulse duration of the light and the analyzer subtracts the light received at the ultra-short pulse duration from the light received at the second pulse duration.

4. The inspection system of claim 3, wherein the second pulse duration is less than 1 picosecond.

5. The inspection system of claim 3, wherein the analyzer compares the difference between the light received at the ultra-short pulse duration and the light received at the second pulse duration to a standard.

6. The inspection system of claim 1 further comprising:

a database, the database storing a standard representative of the light received at the ultra-short pulse duration subtracted from the light received at the second pulse duration for an appropriately patterned reticle.

7. The inspection system of claim 1, wherein the ultra-short pulse duration is less than 1 picosecond.

8. A method of inspecting a reticle associated with manufacture of an integrated circuit, the method comprising:

providing radiation at a first pulse duration to the reticle;

receiving the radiation at the first pulse duration reflected from the reticle;

providing radiation at a second pulse duration to the reticle; and receiving the radiation at the second pulse duration reflected from the reticle, wherein the reticle includes a reflective portion and an absorbing portion, wherein the absorbing portion has similar reflective characteristics at the first and second pulse durations and the reflective portion has different reflective characteristics at the first and second pulse durations.

9. The method of claim 8 further comprising:

comparing the radiation received at the second pulse duration to the radiation received at the first pulse duration.

10. The method of claim 9, wherein the comparing step includes subtraction.

11. The method of claim 8, further comprising:

comparing the radiation received at the second pulse duration to the radiation received at the first pulse duration.

12. The method of claim 11, wherein the reflective portion has similar reflective characteristics at the first and second pulse durations.

13. A method of inspecting a reticle associated with manufacture of an integrated circuit, the method comprising:

providing radiation at a first pulse duration to the reticle;

receiving the radiation at the first pulse duration reflected from the reticle;

providing radiation at a second pulse duration to the reticle; and receiving the radiation at the second pulse duration reflected from the reticle, wherein the reticle includes a reflective portion and an absorbing portion, wherein the absorbing portion has different reflective characteristics at the first and second pulse durations and the reflective portion has similar reflective characteristics at the first and second pulse durations.

14. A method of inspecting a reticle associated with manufacture of an integrated circuit, the method comprising:

providing radiation at a first pulse duration to the reticle;

receiving the radiation at the first pulse duration reflected from the reticle;

providing radiation at a second pulse duration to the reticle; and receiving the radiation at the second pulse reflected from the reticle, wherein the reticle includes a reflective portion and an absorbing portion, wherein the reticle includes a multilayer, wherein intensity of the reflected radiation from the absorbing portion is different at the first pulse duration than at the second pulse duration.

15. The method of claim 8, wherein the radiation is provided by a frequency doubled laser.

16. An inspection system for an EUV reticle for use in an integrated circuit fabrication system, the inspection system comprising:

means for providing radiation at a first pulse duration to the reticle and at a second pulse duration, the first pulse duration being an ultra-short pulse duration; and means for detecting the radiation at the first pulse duration reflected off the reticle, wherein the reticle includes an absorber and a reflector, the absorber having different reflective characteristics at the first and second pulse durations and the reflector having similar reflective characteristics at the first and second pulse durations.

17. The inspection system of claim 16 further comprising:

means for comparing the reflected radiation at the first pulse duration to the reflected radiation at the second pulse duration.

18. The inspection system of claim 17, wherein the means for comparing further comprises:

means for subtracting the reflected radiation at the first pulse duration from the reflected radiation of the second pulse duration.

19. The inspection system of claim 18 further comprising:

means for comparing the subtracted radiation to a standard.

20. The inspection system of claim 16, wherein the reticle includes a multilayer.

* * * * *